United States Patent [19]

Vlasbloem

[11] Patent Number: 5,058,149
[45] Date of Patent: Oct. 15, 1991

[54] EQUIPMENT FOR SLIT RADIOGRAPHY

[75] Inventor: Hugo Vlasbloem, Maasland, Netherlands

[73] Assignee: B.V. Optische Industrie "De Oude Delft", Delft, Netherlands

[21] Appl. No.: 466,343

[22] PCT Filed: Aug. 24, 1988

[86] PCT No.: PCT/EP88/00784
§ 371 Date: Feb. 27, 1990
§ 102(e) Date: Feb. 27, 1990

[87] PCT Pub. No.: WO89/02645
PCT Pub. Date: Mar. 23, 1989

[30] Foreign Application Priority Data
Sep. 7, 1987 [NL] Netherlands ............... 8702113

[51] Int. Cl.⁵ .................. G21K 1/02; G21K 1/04
[52] U.S. Cl. ........................ 378/146; 378/145; 378/147; 378/148; 378/152
[58] Field of Search .......... 378/145, 146, 147, 148, 378/152, 149, 150, 151, 153

[56] References Cited

U.S. PATENT DOCUMENTS 4,675,893  6/1987  Duinker et al. ............ 378/146
4,715,056  12/1987 Vlasbloem et al. ........ 378/146
4,890,312  12/1989 Duinker ..................... 378/146

Primary Examiner—Edward P. Westin
Assistant Examiner—Don Wong
Attorney, Agent, or Firm—Louis E. Marn

[57] ABSTRACT

A body is scanned by a fan-shaped X-ray beam for an X-ray shadow image. Per sector of the fan-shaped X-ray beam detection means deliver a signal which is a measure of the quantity of X-ray radiation instantaneously transmitted in the respective sector through the body. An attenuation device operates in conjunction with a slit-type diaphragm and regulates the quantity of X-ray radiation transmitted under the control of control signals per sector of the fan-shaped X-ray beam. The control signals are formed on the basis of the signals from the detection means. The attenuation device comprises one or more elastic X-ray radiation absorbing strips extending essentially parallel to the slit-type diaphragm. The attenuation device comprises controllable drive members to bring the strip or strips to an undulated state.

20 Claims, 2 Drawing Sheets

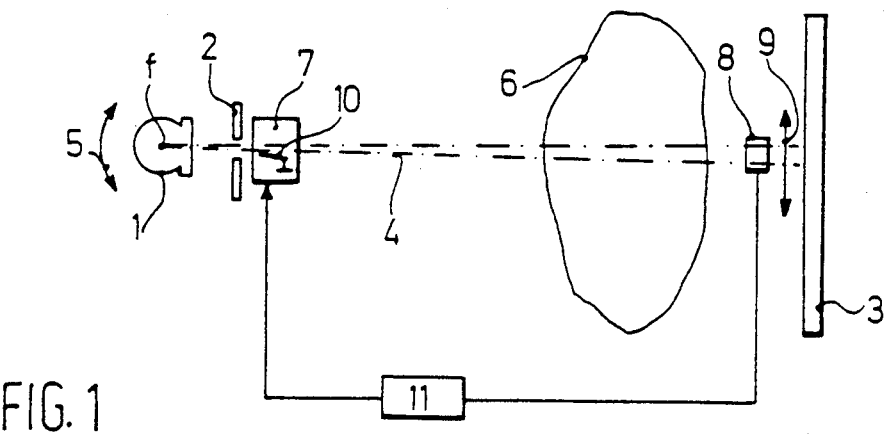
FIG. 1
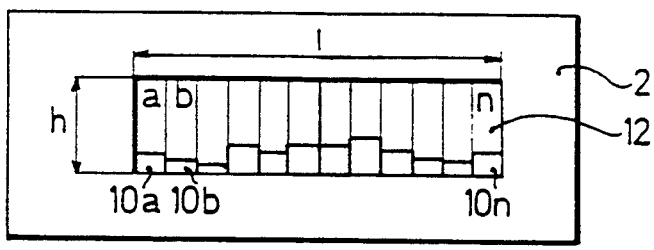
FIG. 2
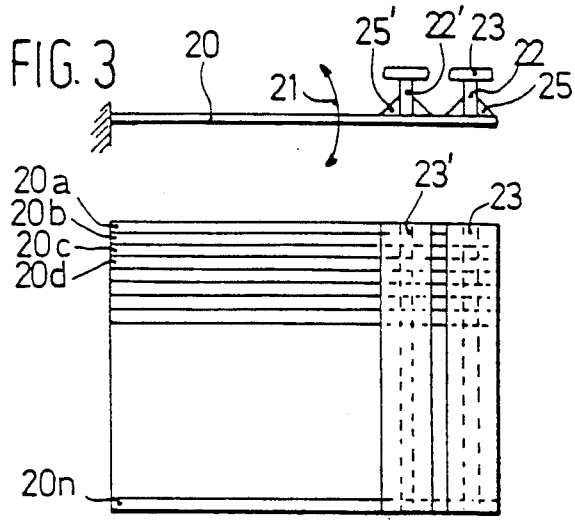
FIG. 3
FIG. 4
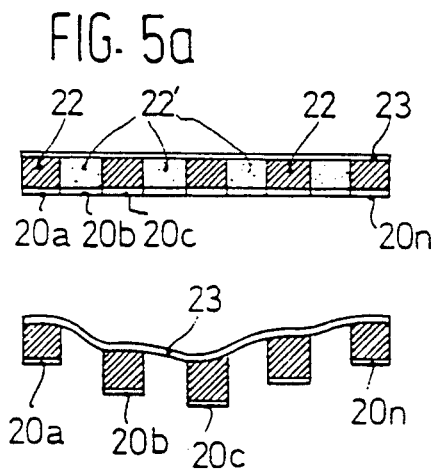
FIG. 5a
FIG. 5b

EQUIPMENT FOR SLIT RADIOGRAPHY

The invention relates to an equipment for slit radiography comprising an X-ray source which can scan a body under examination with a fan-shaped X-ray beam via a slit of a slit-type diaphragm to form an X-ray shadow image; an X-ray detector for receiving the X-ray radiation transmitted through the body; detection means which are equipped to deliver continuously, per sector of the fan-shaped X-ray beam, a signal which is a measure of the quantity of X-ray radiation instantaneously transmitted in the respective sector through the body under examination; control means which form control signals on the basis of the signals from the detection means: and an attenuation device which operates in conjunction with the slit-type diaphragm and which regulates the quantity of X-ray radiation transmitted under the control of the control signals per sector of the fan-shaped X-ray beam.

Such an equipment is known from Dutch Patent Application 8400845. Dutch Patent Application 8400845 describes various exemplary embodiments of suitable attentuation devices which all comprise a number of attenuation elements which cover sharply defined regions, situated next to each other, of the slit diaphragm and which are each able to move, essentially independently of the adjacent attenuation elements, transversely to the longitudinal direction of the slit of the slit diaphragm under the influence of suitable control signals, and extend to a greater or lesser degree into the fan-shaped X-ray beam in the process.

In practice it has emerged that, in certain circumstances which depend essentially on the nature of the body under examination, strip-like artefacts may occur in the X-ray shadow image to be formed.

The object of the invention is to prevent the occurence of such strip artefacts in X-ray shadow images produced with the aid of an equipment for slit radiography of the type described above.

For this purpose, such an equipment for slit radiogaphy is characterized, according to the invention, in that the attenuation device comprises an elastic strip of X-ray radiation-absorbing material, which strip extends, in the rest position essentially parallel to the slit of the slit diaphragm and, during operation, can be brought to an undulated state by controllable drive members. The invention will be described in more detail below with reference to the accompanying drawing.

FIG. 1 shows diagrammatically an equipment for slit radiography;

FIG. 2 shows diagrammatically a front view of the slit diaphragm;

FIGS. 3, 4 and 5 illustrate diagrammatically a first exemplary embodiment of an attenuation device according to the invention in side, plan and front view;

Figure 8:
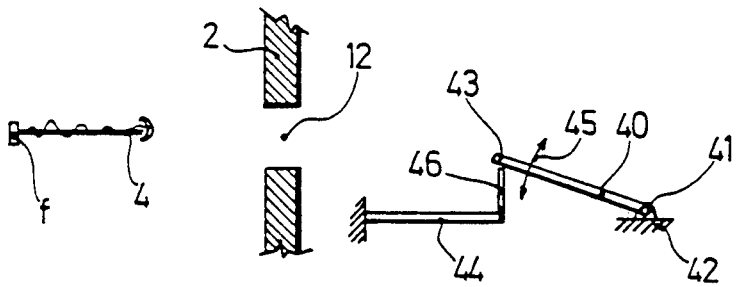
Figure 9:
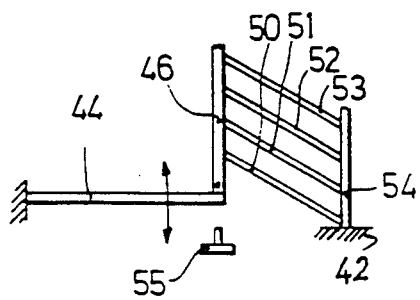
Figure 10:
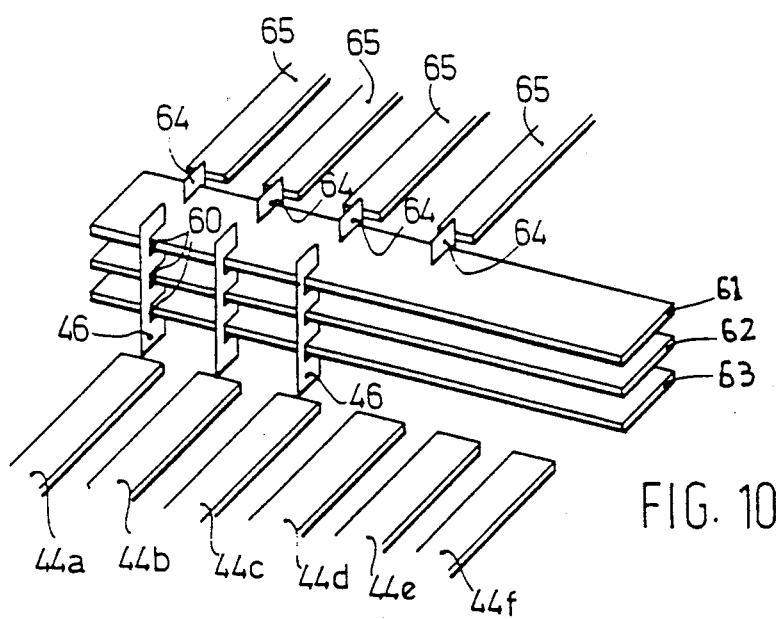

FIGS. 8 to 10 inclusive illustrate another elaboration of the inventive idea and two variants thereof. FIG. 1 shows diagrammatically an example of an equipment for slit radiography comprising an X-ray source 1, a slit diaphragm 2 placed in front of the X-ray source, and an X-ray screen 3. The slit diaphragm 2 transmits a fan-shaped X-ray beam 4 with a relatively small thickness. In operation, the X-ray source and/or the slit diaphragm are moved in a manner such that the X-ray beam 4 scans the X-ray detector 3. For this purpose, for example, the X-ray source may be swivelled together with the slit diaphragm about an axis extending transversely to the plane of the drawing through the X-ray focus f, as indicated by an arrow 5. If a body 6 to be irradiated is situated between the X-ray source and the X-ray detector, a radiograph can be made in this manner of (a part of) the body 6. Attention is drawn to the fact that, instead of a stationary X-ray detector, a strip-type X-ray detector can be used in the manner as described in Dutch Patent Application 8303156.

In order to be able to influence the quantity of X-ray radiation transmitted through the slit diaphragm per sector of the fan-shaped X-ray beam to make an equalized radiograph, a controllable attenuation device 7 operating in conjuction with the slit diaphragm is present. The attenuation device comprises adjacent sectors of attenuation elements 10 which influence the fan-shaped X-ray beam. The attenuation elements may be constructed in diverse manners, as described, for example, in Dutch Patent Application 8400845. In the example shown in FIG. 1, the attenuation elements are of tongue type and the free ends of the tongues are able to be swivelled under the influence of suitable control signals to a greater or lesser extent into the x-ray beam. The attenuation elements may, however, also be of slide type, for example, as also described in Dutch Patent Application 8400845.

To generate the control signals needed for the attenuation device, there is situated beyond the body 6 to be irradiated a detector which detects the radiation transmitted through the body 6 per sector of the X-ray beam and generates corresponding electrical signals. The detector may comprise a series of light detectors which are situated behind the X-ray screen level with the incident beam and which detect the quantity of light generated by the X-ray screen 3 under the influence of the incident X-ray radiation. It is also possible to detect the X-ray radiation transmitted through the X-ray screen 3. The detector may also be situated in front of the X-ray screen and may then comprise, for example, an oblong dosimeter, as is described in the Applicant's Dutch Patent Applications 8503152 and 8503153.

Such a dosimeter is indicated diagrammatically at 8 in FIG. 1 and is moved synchronously along with the scanning X-ray beam, as indicated by an arrow 9. The signals originating from the dosimeter are fed to a control circuit 11 which forms the control signals for the attenuation elements.

FIG. 2 shows diagrammatically a view of the slit diaphragm 2 seen from the X-ray source. The diaphragm has a slit 12 having a height h and a length l. The diaphragm slit is divided in the longitudinal direction into a number of regions a, b . . . n which match corresponding sectors of the X-ray beam 4 and which each form the working region of attenuation elements 10a, 10b . . . 10n. The attenuation elements are in this example placed behind the slit diaphragm, but they may also be situated in front of the slit diaphragm. Moreover, several sets of attenuation elements may be used which may be moved possibly both from below and from above into the X-ray beam.

The attenuation elements may be of slide type or tongue type or a combination of the two and can move in a direction transverse to the longitudinal direction of the slit. The attenuation elements therefore influence locally the instantaneous effective height of the slit 12 of the slit diaphragm. As can be seen in FIG. 2, which shows a possible instantaneous position of the attenuation elements, at least one of the effective longitudinal edges of the slit acquires, during operation, a stepped form as a result of the operation of the attenuation elements.

In practice it has emerged that, as a result of this, strip-type artefacts may be produced in certain conditions in the X-ray shadow image to be formed.

According to the invention, strip-like artefacts, which are the consequence of the variation during operation of the stepped form of at least one of the effective longitudinal edges of the slit of the slit diaphragm, can be prevented by using an elastic strip of X-ray-absorbing material fitted over the ends, which extend into the X-ray beam, of the attenuation elements.

FIGS. 3 and 4 show diagrammatically, in side view and plane view, a first exemplary embodiment of an attenuation device according to the invention and FIG. 5 shows the same attenuation device in front view in the rest position (a) and in the operating position (b). In the example shown, the attentuation device comprises a number of tongues $20a \ldots 20n$, which are mounted next to each other in cantilever manner and which may be, for example, piezoelectric tongues, as described in Dutch patent applications 8400845 and 8503151. The free ends of the tongues are able to move up and down under the control of the control device 11, as indicated by an arrow 21.

In this example, each tongue is provided at the free end with an absorption element 22 extending transversely to the longitudinal direction of the tongue and in the direction of movement of the end of the tongue.

The absorption elements may, for example, be small tungsten plates or small tantalum plates. With such an attenuation device it is possible to achieve the situation shown in FIG. 2. The same is true for the case where the small plates are constructed as slides and are not mounted on the ends of tongues. Preferably, each absorption element 22 comprises two small plates, placed behind each other, of different, X-ray-absorbing material. In this connection, the two materials can be chosen in a manner such that the K-shells overlap, such as, for example, is the case for tantalum and lead.

A narrow elastic strip 23 of X-ray-absorbing material is fitted over the tops of the absorption elements. Such a narrow strip may in practice have, for example, a thickness of approx. 0.25 mm and a width of approximately 1.5 mm for a slit height h of approx. 2 mm, and may be manufactured from silicone rubber-containing tungsten powder. The narrow strip may be glued onto the absorption elements, while the absorption elements may be glued into small holders 25, 25' of, for example, plastic, which small holders are glued to the tongues.

As a result of using such a narrow absorption strip 23, instead of the stepped contour, shown in FIG. 2, of the combined attenuation elements, a flowing contour is produced as shown in FIG. 5b.

Since, when viewed in the longitudinal direction of the slit, the absorption elements 22 should be immediately adjacent to each other, the narrow elastic strip prevents a marked difference in height between two adjacent absorption elements if the absorption elements are all in one row. In order to prevent this effect, use may advantageously be made of an arrangement of the absorption elements 22 which is staggered turn and turn about, a set of absorption elements 22 in each case alternating with absorption elements 22' placed more to the front or to the rear, as shown in FIGS. 3 to 5 inclusive.

A second narrow strip 23' is fitted over the elements 22'. For the sake of clarity, FIG. 5b shows only the tongues 20a, 20c etc. and the narrow strip 23 fitted on the associated absorption elements.

Figure 6:
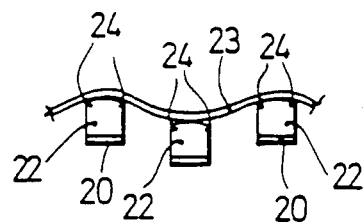
FIG. 6 shows diagrammatically a modification of the device of FIGS. 3 to 5 inclusive.

Preferably, the top corners of the absorption elements 22 are to some extent rounded off, as is indicated in FIG. 6 at 24. As a result of this, the narrow strip is better able to follow the contour determined by the position of the absorption elements and the risk of damage of the narrow strip at the position of the corners is less.

According to another elaboration of the inventive idea, the assembly of an elastic strip and the even or odd absorption elements can be combined into a single elastic absorption member.

Figure 7:
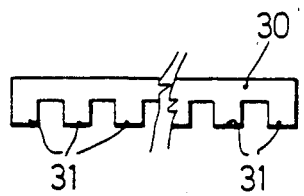
FIG. 7 illustrates another elaboration of the invention idea.

FIG. 7 shows such a combined absorption member which comprises a strip-type part 30 which is provided with teeth 31. The strip-type part corresponds to the narrow strip 23 or 23', while the teeth correspond to the absorption elements 22 or 22'. A complete attenuation device should therefore comprise two such comb-like absorption members which are coupled respectively to the even and the odd tongues or other drive members.

A comb-like member, such as that shown in FIG. 7, may be manufactured, for example, by casting silicone rubber mixed with tungsten powder and lead powder and a suitable curing agent in a mould. The comb-like absorption member thus obtained after curing may then be glued by means of the teeth 31 to the even or odd tongues.

It is pointed out that, in the example shown, the teeth 31 are just as wide as the intervening spaces between the teeth. If desired, the intervening spaces may have a width which is a multiple of the width of the teeth. If, for example, the intervening spaces are twice as wide as the teeth, three absorption members placed in a staggered manner behind each other are necessary for a complete attenuation device.

In a similar manner, three or more narrow strips can be used instead of two narrow strips 23 and 23' in the case shown in FIGS. 3 to 5 inclusive.

FIG. 8 shows another elaboration of the inventive idea in which the attenuation device comprises a relatively wide elastic strip 40 of X-ray-absorbing material, such as silicone rubber containing tungsten powder and/or tantalum powder and/or lead powder. The elastic strip extends parallel to the slit 12 of the slit diaphragm. One of the longitudinal edges 41 is fixed with the aid of means suitable for the purpose, for example, glued to a carrier 42. The other longitudinal edge 43 is coupled to drive members which are attached to the edge 43 at a certain mutual intermediate distance regularly distributed over the length of the strip. The drive members may advantageously comprise piezoelectric tongues 44 which are mounted in cantilever manner and the free ends of which carry coupling members 46 which couple said ends to the edge 43 of the strip 40 so that a movement of the ends of the tongues is transferred to the edge 43 of the strip as is indicated by an arrow 45.

The ends of the tongues or other controllable drive members themselves always remain outside the X-ray beam 4. However, the coupling members 46 do extend during operation into the X-ray beam and should therefore be manufactured from material which does not, or virtually does not, attenuate X-ray radiation. The coupling members may be composed, for example, of somewhat flexible small rubber rods or strips which are glued to the ends of the tongues or of small rods or the like or plastic such as mylar.

During operation, the strip 40 assumes an undulated form at least at the edge 43, the edge 43 extending locally to a greater or lesser degree into the X-ray beam.

FIG. 9 shows a variant of FIG. 8 in which, instead of a single strip 40 of X-ray radiation-absorbing material a number of such strips is placed above each other. In the example shown, four strips 50 to 53 inclusive are used, one edge of which is in each case joined by means of a coupling member 46 to a drive member 44, the other edges being joined to a fixed carrier 42 and second coupling members 54 fitted at regular intervals. If the coupling member 46 is moved downwards from the operation position shown, the absorption of the X-ray radiation decreases. The absorption is lowest if the strips 50 to 53 inclusive extend parallel to the direction of the X-ray radiation. In order to avoid overshoot past said position, a diagrammatically shown, adjustable stop member 55, for example an adjustment screw, is present.

FIG. 10 shows in perspective a variant of the exemplary embodiment shown in FIG. 9 in which the second coupling members are likewise joined to controllable drive members. The maximum deflection needed in total of each drive member is halved as a result of this, which in principle makes a more rapid control possible.

FIG. 10 shows a number of piezoelectric tongues 44a ... 44f which are situated next to each other and which correspond to the tongues 44 shown in FIGS. 8 and 9, and the coupling members 46 which are joined, for example, by gluing or by a rubber hinge to the ends of the tongues 44 and which are composed in this example of vertically situated strips of, for example mylar, which are provided with notches 60 which each engage around one longitudinal edge of an absorption strip 61, 62, 63 and may be bent for reinforcement, for example in a V shape.

Fitted at the other longitudinal edges of the absorption strips are similar coupling members 64 which are each joined to one of a second set of drive members 65. The second set of drive members acts in opposition to the first set and in this example is composed, like the first set of drive members, of piezoelectric tongues, but other suitable drive members, such as sprung tongues, sliding members, stepping motors and the like may also be used.

Attention is drawn to the fact that, after the above exposition, diverse modifications are obvious to the person skilled in the art. Thus, for example, a narrow absorbing strip can be fitted directly onto the ends of piezoelectric tongues or other tongues. Such modifications are deemed to fall within the scope of the invention.

I claim:

1. A slit radiographic assembly comprising:
    an X-ray source for scanning a body under examination with a fan-shaped X-ray beam via a slit of a slit-type diaphragm to form an X-ray shadow image;
    an X-ray detector for receiving X-ray radiation transmitted through said body;
    detection means for delivering continuously, per sector of the fan-shaped X-ray beam, a signal measuring quantity of X-ray radiation instantaneously transmitted per sector through said body under examination;
    control means forming control signals based on said signals from said detection means; and
    an attenuation device operating in conjuction with said slit-type diaphragm for regulating the quantity of X-ray radiation transmitted under the control of the control signals per sector of said fan-shaped X-ray beam, said attenuation device comprising absorption elements and an elastic strip of X-ray radiation-absorbing material extending in a rest position parallel to said slit of said slit diaphragm and mounted on drive members.

2. The slit radiographic assembly according to claim 1 wherein said elastic strip of X-ray radiation-absorbing material is joined to said plates constituting said absorption elements.

3. The slit radiographic apparatus according to claim 2 wherein said plates are alternately positioned in a first plane and a second plane and wherein a first elastic strip of X-ray radiation-absorbing material is fitted over said plates in said first plane and a second elastic strip of X-ray radiation-absorbing material is fitted over said plates in said second plane.

4. The slit radiographic apparatus according to claim 2 or 3 wherein said plates have rounded-off corners in contact with said elastic strip of X-ray radiation-absorbing material.

5. The slit radiographic apparatus according to claim 2, 3 or 4 wherein a number of plates of different X-ray absorbtion material are successively placed in a direction of X-ray radiation.

6. The slit radiographic apparatus according to claim 5 wherein said plates of the different X-ray absorbtion material overlap each other.

7. The slit radiographic apparatus according to claim 3 wherein said plates and associated elastic strip of X-ray radiation-absorbing material are of one piece construction as a comb-like.

8. The slit radiographic apparatus according to claim 7 wherein said comb-like absorption member is manufactured by casting in a mould a suitable elastic material and powder of X-ray radiation-absorbing material.

9. The slit radiographic apparatus according to claim 1 or 2 wherein said drive members are tongues of piezoelectric material.

10. The slit radiographic apparatus according to claim 1 wherein said elastic strip of X-ray radiation-absorbing material is joined by means of a first longitudinal edge to a number of coupling members essentially transparent to X-ray radiation moveable essentially transversely to a longitudinal direction of said slit.

11. The slit radiographic apparatus according to claim 10 wherein said elastic strip of X-ray radiation-absorbing material is attached by a second longitudinal edge to a solid carrier extending parallel to said slit.

12. The slit radiographic apparatus according to claim 10 wherein at least one additional elastic strip of X-ray radiation-absorbing material extends with an intervening space parallel to said first elastic strip of X-ray radiation-absorbing material having a first longitudinal edge which, together with a corresponding first longitudinal edge of said first elastic strip of X-ray radiation-absorbing material, is joined to a number of first coupling members, and wherein said second longitudinal edges are joined to a number of second coupling member essentially transparent to X-ray radiation, and wherein at least said first coupling members are joined to a corresponding set of first drive members movable essentially transversely to said longitudinal direction of said slit.

13. The slit radiographic apparatus according to claim 12 wherein said second coupling members are stationary.

14. The slit radiographic apparatus according to claim 12 said second coupling members are joined to a corresponding set of second drive members acting in opposition to said first set of drive members.

15. The slit radiographic apparatus according to claim 12, 13 or 14 wherein said coupling members are manufactured from strips of stiff plastic material which essentially does not absorb X-ray radiation, each strip of X-ray radiation-absorbing material being provided with notches which each engage round the longitudinal edge of an absorbing strip.

16. The slit radiographic apparatus according to claim 10, 11, 12, 13, 14 or 15 wherein said elastic strip(s) of X-ray radiation-absorbing material is (are) manufactured from silicone rubber containing an X-ray radiation-absorbing powder.

17. The slit radiographic apparatus according to claim 16 wherein said X-ray radiation-absorbing powder comprises tungsten powder.

18. The slit radiographic apparatus according to claim 16 wherein said X-ray radiation-absorbing powder comprises tantalum powder.

19. The slit radiographic apparatus according to claim 16 wherein said X-ray radiation-absorbing powder comprises lead powder.

20. The slit radiographic apparatus according to claim 12, 13, 14 or 15 wherein said drive members are piezoelectric tongues.

* * * * *